United States Patent [19]

Hatch et al.

[11] Patent Number: 5,100,575
[45] Date of Patent: Mar. 31, 1992

[54] THERMALLY STABLE, REACTIVE ORGANOMETALLIC COMPOSITIONS CONTAINING COPPER

[75] Inventors: Helen B. Hatch, Kings Mountain; Robert S. Wedinger, Gastonia, both of N.C.

[73] Assignee: FMC Corporation, Philadelphia, Pa.

[21] Appl. No.: 474,194

[22] Filed: Feb. 2, 1990

Related U.S. Application Data

[63] Continuation-in-part of Ser. No. 404,820, Sep. 8, 1989, abandoned.

[51] Int. Cl.$^5$ .............................................. C09K 3/00
[52] U.S. Cl. ................................................. 252/182.3
[58] Field of Search ..................................... 252/182.3

[56] References Cited

U.S. PATENT DOCUMENTS

| | | | |
|---|---|---|---|
| 3,872,101 | 3/1975 | Siddall et al. | 260/326.5 E |
| 4,701,499 | 10/1987 | Torelli et al. | 514/175 |
| 4,814,327 | 3/1989 | Ottow et al. | 514/179 |
| 4,952,710 | 8/1990 | Babiak et al. | 549/416 |

OTHER PUBLICATIONS

Lindstedt, E.; Nilsson, M., Acta Chemica Scandinavica B., 40, 466–469, (1986); *2-Thienyl as Auxiliary Group in Mixed Lithium Diorganocuprates.*
Lindstedt, E.; Nilsson, M. Olsson, T., J. Organometallic Chem., 334, 255–61, (1987); *From 2-Thienylcopper Couplings to Trimethylsilyl-promoted Organocopper Additions.*
Malmberg, H.; Nilsson, M; Ullenius, C.; Tetrahedron Lett., 23(37), 3823–26, (1982), *Stereoselectivity in the Transfer of the 2-(1-dimethylaminoethyl)phenyl Group, R\*, From LiR$_2$Cu and Li(R\*)(2-thienyl)Cu to Enones.*
Andersson, S.; Jagner, S.; Nilsson, M.; Urso, F., J. Organometallic Chem., 301, 257–67, (1987); *Steric Consequence of the Diastereoselective Addition of Chiral Lithium 2-(1-dimethylaminoethyl)phenyl Cuprates to Some Enones.*
Lipshutz, B. H.; Koerner, M.; Parker, D. A., Tetrahedron Lett., 28(9), 945–48, (1987); *2-Thienyl(cyano)copper Lithium, A Lower Order, Stable "Cuprate in a Bottle" Precursor to Higher Order Reagents.*
Martin, S. F.; Fishpaugh, R. R.; Power, J. M.; Giolando, D. M.; Jones, R. A.; Nunn, C. M.; Cowley, A. H., J. Am. Chem. Soc., 110, 7726–28, (1988); *Structure and Reactivity of Novel Lithium Di–tert–butylphosphido(alkyl)cuprates.*
Bertz, S. H.; Dabbagh, G.; J. Chem. Soc., Chem. Commun., 1030, (1982); *Factors Governing the Thermal Stability of Organocopper Reagents. Two New Classes of Heterocuprates with Greatly Improved Thermal Stability.*
Bertz, S. H.; Dabbagh, G; J. Org. Chem., 49, 1119, (1984); *Dicyclohexylphosphide as an Auxiliary Ligand for Thermally Stable Heterocuprates with Considerably Improved Reactivity. Some Beneficent Effects of LiBr on Cuprate Reactivity.*

Primary Examiner—Edward A. Miller
Attorney, Agent, or Firm—Charles C. Fellows; Robert L. Andersen

[57] ABSTRACT

An organometallic composition containing copper(I) comprising:
(a) an organometallic composition of the formula $$R_T R_R CuLi$$

where $R_T$ is a transferable anionic group, $R_R$ is a residual anionic group and containing 0.01 to 1.2 mole equivalents of halide in the form of chloride, bromide or iodide; 0 to 0.12 mole equivalents of magnesium; 0.5 to 7 mole equivalents of a Lewis base and a solvating amount of a liquid hydrocarbon.

42 Claims, No Drawings

THERMALLY STABLE, REACTIVE ORGANOMETALLIC COMPOSITIONS CONTAINING COPPER

This application is a continuation-in-part of Ser. No. 404,820, filed Sept. 8, 1989.

This invention concerns thermally stable organocuprate compositions and methods of their preparation.

Recently, there has been increased interest in copper promoted reactions of metalated alkyls for use in drug synthesis and general organic synthesis. The presence of a copper(I) salt in the reaction changes the regiochemistry of the reaction of an alkyllithium with many organic substrates. Before 1966, copper promoted conjugate addition reactions were effected using the Grignard reagent and a catalytic amount of a copper(I) salt. In 1966, H. O. House et al. in the J. Org. Chem., 31, 3128 (1966); and also E. J. Corey and G. H. Posner in the J. Am. Chem. Soc., 89, 3911, (1967); b. 90, 5615, (1968) studied the reaction of stoichiometric organocopper reagents (0.5 or more equivalents of copper(I) salt per equivalent of R—), with alpha, beta-unsaturated carbonyl compounds. These "cuprate" reagents ($R_2CuLi$) referred to as homocuprates where R=R, were found to produce higher yields and greater stereoselectivity than combinations of the Grignard and catalytic amounts of copper(I) salt. See also G. H. Posner, Organic Synthesis, 19, 1-113 (1972).

Since 1966, organocuprates have become one of the most useful reagents for carbon-carbon bond formation. In spite of their utility in organic synthesis, use of cuprates on a large scale (e.g. for drug and natural products synthesis on a plant scale) has been limited. This is due to (1) their extreme thermal instability (decomposing above $-30°$ C.); and (2) the fact that homocuprates ($R_2CuLi$) transfer only one R group to a substrate wasting one R group.

The present invention provides stable hydrocarbon soluble organometallic compositions containing copper(I) of the general formula $R_T R_R CuLi$ wherein $R_T$ is a transferable anionic group, $R_R$ is a residual anionic group, and $R_T$ is selected from lower alkyl radicals containing 1 to 10 carbon atoms, aryl radicals of 6 to 24 carbon atoms, and while $R_R$ is selected from aryl, furyl and thienyl and other unsaturated radicals and containing:

(a) 0.01 to 1.2 mole equivalents halide in the form of chloride, bromide or iodide,
(b) 0 to 0.12 mole equivalents magnesium,
(c) 0.5 to 7 mole equivalents Lewis base,
(d) a solvating amount of liquid hydrocarbon,
(e) wherein the mole ratios of total anionic organic groups ($R_T + R_R$), to copper and lithium minus the equivalents of halide is within the following ranges:
  1. ($R_T + R_R$): Cu equivalents = 1:0.4 to 1:0.6
  2. ($R_T + R_R$): Li (Total Li equivalents—halide equivalents) = 1:0.4 to 1:0.6 and
(f) wherein the mole ratios of total anionic organic groups $R_T + R_R$), to total lithium is within the following range:

$R_T + R_R$) : Total Li equivalents = 1:0.4 to 1:1.2

These organometallics are generally prepared in liquid mixtures of Lewis bases mixed with hydrocarbons, such as, mixtures of ethers with aromatic, aliphatic and cycloaliphatic hydrocarbons, such as tetrahydrofuran with toluene. A typical preparation involves reacting an alkyllithium compound, ($R_T Li$) such as methyllithium (MeLi), with a copper halide such as $CuBr.Me_2S$, at a temperature below $-30°$ C. to form an alkyl copper which is reacted with an unsaturated $R_R Li$ compound such as thienyllithium, and with $R_T Li$ compound (e.g., methyllithium) to form the $R_T R_R CuLi$ compound, for example, a lithium alkyl thienyl cuprate. As used herein Me=methyl.

These organometallic compositions comprise: (1) an organometallic composition of the formula $R_T R_R CuLi$; (2) 0 to 0.12 mole equivalents of magnesium; (3) 0.5 to 7 mole equivalents of Lewis base per mole of organometallic composition; (4) a solvating amount of hydrocarbon solvent; and (5) 0.01 to 1.2 moles of lithium halide, LiX, based on the organometallic composition.

The organometallic heterocuprates compositions, of this invention have utility in regioselective addition reactions of unsymmetrical unsaturated substrates; they tend to be regiospecific, that is when two different addition products are possible, only one product is formed. These heterocuprates contain two different carbanions: one is transferred to the substrate ($R_T$) and the other remains bound to copper ($R_R$). $R_R$ can be chosen as to give the greatest stability to the cuprate complex. The general reaction of a heterocuprate with a substrate is shown in Equation 1.

$$R_T R_R CuLi + S \rightarrow R_T - S^- + Li^+ + R_R Cu \qquad (1)$$

For example, when the substrate is an alpha, beta-unsaturated ketone as shown in Equation 2, the reaction proceeds as indicated:

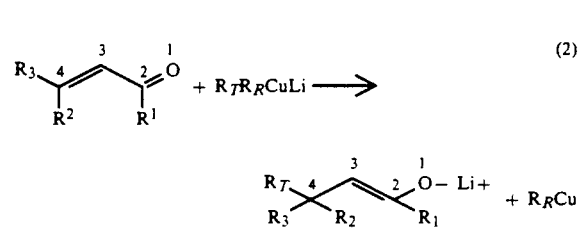

(2)

wherein R is alkyl, $R_T$ is the transferred carbanion and $R_R$ is the retained carbanion. If methyllithium had been employed in place of the heterocuprate the addition reaction would have proceeded as follows:

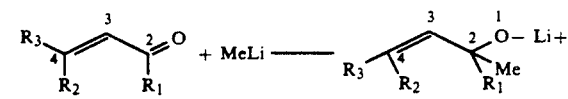

The positions on the substrate are numbered 1 to 4. Methyllithium adds the methyl group to the 2 position, while in the copper promoted reaction, the methyl group adds to the 4 position. The reactions are called 1,2 and 1,4 additions, respectively, because lithium coordinates with the oxygen in an intermediate step (not shown). 1,4-addition is also called conjugate addition because the $R_T$ group adds to one end of the conjugated system while the lithium metal is coordinated at the other.

The use of a heterocuprate for 1,4 addition wherein $R_T$ is an expensive chiral anion and $R_R$ is an inexpensive stabilizing ligand such as thienyl is contemplated. In this case the cuprate could efficiently transfer the expensive anion whereas the homocuprate ($R_2CuLi$) would only transfer less than 50% of the anion.

Since organocopper compounds ($R_RCu$ in equation 2) are insoluble in most solvents, the process is contemplated where $R_RCu$ such as thienylcopper (I) could be recovered and reused, for instance to form another cuprate solution.

In 1986, E. Linstedt and M. Nilsson in the Acta Chemica Scandinavica B, 40, 466, prepared a Me(2-thienyl)CuLi composition. However, they found that this composition did not react with 2-cyclohexenone.

Cuprate solutions of homocuprates of the formula $R_2CuLi$ are prepared by addition of an alkyllithium to cuprous halide, as shown in the general equation number (3).

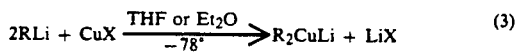

$$2RLi + CuX \xrightarrow[-78^\circ]{\text{THF or Et}_2\text{O}} R_2CuLi + LiX \quad (3)$$

The reactions take place in THF or ether at low temperatures. In most cases they are formed in situ and used immediately due to the extreme instability of the cuprate. Heterocuprates may be prepared by sequential addition of two different alkyl- or aryllithium reagents to a cuprous halide. The order of addition varies, but the product is the same.

The by-products of the reaction, lithium halide and $Me_2S$ (from $CuBr.Me_2S$ complex) remain in solution and are separated on workup.

The heterocuprates of the present invention can be prepared by reacting a copper(I) complex or salt, such as a copper halide complex, with an alkyl, or phenyl lithium, $R_TLi$, at $-78°$ to $0°$ C. to form an organocopper compound $R_TCu$. The $R_TCu$ compound is then reacted with an unsaturated or aromatic organo lithium compound, $R_RLi$ to form the desired $R_TR_{Rpl} CuLi$ organocuprate. The reaction can be done by first forming an $R_RCu$ compound which is then reacted with an $R_TLi$ compound to form the $R_TR_RCuLi$ heterocuprate.

A better process for preparation of the cuprate $R_TR_RCuLi$ is to mix $R_TLi$ and $R_RLi$ to form a solution or suspension in Lewis base and aromatic solvent, then react the mixture with a copper(I) complex. The temperature of the reaction may range from $-60°$ to $50°$. This process is more commercially useful because it allows one to prepare the cuprate at ambient temperatures. If the organocopper complex is formed first, then the organolithium added, as in the two step procedure outlined above, the reaction must be kept cold ($-78°$ to $0°$ C.) because of the thermal instability of the organocopper complexes ($R_RCu$ and $R_TCu$).

Another process is to prepare $(R_R)_2CuLi$ by either process above, and then react the homocuprate, $(R_R)_2CuLi$, with an alkyllithium ($R_TLi$), to form the desired $R_T(R_R)_2CuLi_2$, a heterocuprate. Heterocuprates formed by this process are described as higher order cuprates and are useful for many of the same reactions that cuprates are used for. Examples of these reactions include 1,4 addition to alpha,beta-unsaturated ketones, epoxide openings, and substitutions of halides. These higher order heterocuprates are not normally stable at ambient temperatures, and must be prepared in situ, yet this process is preferred over other methods because $(R_R)_2CuLi$ (can be stored and transferred more easily than other precursors to higher order cuprates.

The methyl heterocuprate, Me(2-thienyl)CuLi, formed by either the one step reaction at ambient temperatures or the two step reaction at low temperature is thermally stable and has been stored at room temperature without loss of active methyl for $2\frac{1}{2}$ months. As shown in Table 1, this cuprate has far superior stability when compared to the dialkylcuprate or cuprates which do not contain an unsaturated $R_R$ stabilizing ligand. This cuprate is also reactive, having the same reactivity as $Me_2CuLi$ in 1,4 addition to cyclohexenone with no detectable 1,2 addition. Me(2-thienyl)CuLi will also react with 2-cyclohexenone at room temperature to give the 1,4 adduct.

The Lewis bases useful in solvating the heterocuprates of this invention are liquid organo compounds, typically thiophene, ethers such as diethyl ether, tetrahydrofuran, methyltetrahydrofuran, and the like. These Lewis bases are mixed with liquid aromatic hydrocarbons.

Compositions of this invention having good thermal stability can have Lewis base mole ratios (base/$R_T$) which can vary within the range of 0.5 to 7. A ratio of 2 to 6 is more preferable and 2.5 to 5 is generally most preferable. In the case where $R_T$ is methyl, a ratio of 2.5 to 3.5 is most preferable for stability and cost. While thermal stability of these cuprates may be quite good at the lower mole ratio ranges it has been found that during storage lithium halide may precipitate from solution giving the sample a poor appearance. This precipitation does not appear to reduce thermal stability of the cuprate and can be avoided by using a slightly higher Lewis base ratio. For example, when the lithium halide is LiBr, $R_T$ is methyl and $R_R$ is thienyl precipitation of LiBr is avoided by using a base/$R_T$ ratio in the range of 4 to 6. In the case of $R_T$=Me, a ratio of 2.5 to 3.5 is most preferable.

Liquid aromatic solvents useful in practicing this invention include, but are not limited to benzene, toluene, ethylbenzene, o, m & p-xylene, isopropylbenzene (cumene), n-propylbenzene, 1-methyl,3-ethylbezene, 1-methyl, 4-ethylbenzene, 1,3,5-trimethylbenzene (mesitylene), 1-methyl-,2-ethylbenzene, 1,2,4-trimethylbenzene, 1,2,3-trimethylbenzene, n-butylbenzene, s-butylbenzene, t-butylbenzene, 1-methyl-, 4-isopropylbenzene (cymene), 1,2,3,5-tetramethylbenzene, 1-methylnaphthalene, 1,4-dimethylnaphthalene and the like.

The ratio of hydrocarbon solvent, aromatic, aliphatic and cycloaliphatic, and mixtures thereof, to complex could be in the range of 3 to 18.

The concentration can vary in the range 0.1 to 2N in $R_T$; 0.5 to 1.5 is preferable and 1N is most preferable.

The preferred non-transferable organo groups ($R_R$) are heterocyclic unsaturated groups in the cuprates of this invention can include but are not limited to thienyl, furyl, thianaphthyl, thiazoyl, benzothiazoyl, pyridyl, pyrazyl, and pyrimidyl; with the most preferred groups being thienyl. These groups would contain appropriate substituents, for example, but not limited to: alkyl, aryl, alkoxyl, alkyl sulfide (N,N-dialkylamino)alkyl, halo, ethereal alkylsilyl and alkyl halide.

Other less preferable unsaturated non-transferable organic groups ($R_R$) in the cuprates of this invention can include but are not limited to phenyl, alkynyl, and naphthyl, similar groups containing appropriate substituents for example, but not limited to: allyl, phenyl, alkoxy alkylsulfide (N,N,dialkylamino)alkyl, halo, and ethereal.

$R_T$ groups include alkyl to $C_{10}$, aryl to $C_{24}$, and other similar radicals containing appropriate substituents, for example, but not limited to: alkyl, phenyl, alkoxy, alkyl sulfide, halo, and ethereal. This invention includes compositions in which $R_R$ and $R_T$ are the same such as dithienyl cuprates. Most preferred are alkyl to $C_{10}$.

The use of $R_T$ containing Mg2+, for example, most preferred are alkyl to $C_{10}$ MeLi/Me$_2$Mg solutions in THF/cumene containing 0 to 12 mole percent Me$_2$Mg in the preparation of the cuprate is contemplated. For example, mixing MeLi/Me$_2$Mg in THF/cumene with 7% Me$_2$Mg with thienyllithium and subsequent addition of this solution to CuBr.Me$_2$S would produce the composition, Me(2-thienyl)CuLi/]Me(2-thienyl)-Cu]Mg$_2$.

The following Examples and Comparative Examples further illustrate the invention and the preparation of four cuprates. The thermal stability of these cuprates was determined (see Table 1). The reactivity of Me(2-thienyl)CuLi was determined and compared to the commonly used reagent, Me$_2$CuLi. The products were analyzed by NMR, GC (gas chromatography), atomic absorption (AA) spectroscopy, Mohr titration method for halide, and potentiometric titration for halide. An argon atmosphere was maintained over the solutions for all procedures until quenching.

EXAMPLE I

PROCEDURE FOR PREPARATION OF METHYL(2-THIENYL)CuLi AT AMBIENT TEMPERATURES (EXP. #6496, #6487 AND #6495)

Reagents:
4.13 g CuBr.Me$_2$S (20.1 mmole)
28.11 g of a mixture containing:
(13.13 g MeLi 5.28 wt % in the THF/toluene
1.53 g THF
23.51 g Toluene
5.73 g solid thienyllithium.THF etherate (20.22 mmole MeLi, 17.26 mmole ThienylLi use for preparation.)

Procedure:
CuBr Me$_2$S, which had been stored under vacuum, was placed in a 250 ml 3-neck flask. The flask with the CuBr.Me$_2$S was evacuated 4 times to remove air picked up during weighing. The methyllithium/thienyllithium mixture was added quickly to the dry air-free solid. Immediately on addition of the methyllithium/thienyllithium solution, a bright yellow-gold solid formed which dissolved within one minute to leave a gray precipitate. The flask became warm to the touch indicating an exothermic reaction. Over 30 minutes the precipitate darkened to black. The mixture was stirred overnight, then transferred via cannula to a filter funnel. The mixture filtered easily, producing a clear, gold-brown liquid. The product was transferred via cannula to an air tight glass storage flask with a septum inlet.

Yield Me-: 84% (NMR)
Composition: 0.48N Me-, THF/Me- = 3.08
(See Table II for complete composition)

The product solution was stable (see Table 1) and showed no loss of active Me- after storage in air tight storage bottle with a septum inlet for 18 days at room temperature. This example was repeated as #6487 and #6495 and reported on in Table II; and without adding additional THF and toluene to the MeLi/Thienyllithium etherate mixture and is reported in Table II as Exp. #6511.

EXAMPLE II

PREPARATION OF METHYL(2-THIENYL)CuLi AT VARIOUS TEMPERATURES (EXP. #6474 AND #6482)

Methyllithium, 5.28 wt % in THF/toluene was mixed with thienyllithium 11-12 wt % in THF/toluene to form a 1:1=MeLi:ThienylLi (ThLi) solution. This solution is stable to both precipitation and decomposition if stored in the freezer. CuBr.Me$_2$S was placed in a 3-neck flask and flushed with argon. The temperature was adjusted by lowering the flask into a dry ice ($-60°$ C.), salt ice ($-15°$ C.), ice water (0° C.) or no bath (25°-33° C.). Enough of the MeLi/ThLi solution was added to form a mixture containing the ratio of Cu:Me—:-Thienyl$^-$ = 1:1:1. The size of the runs ranged from 7 to 25 mmole Cu. The mixtures were stirred 1-2 hours at the appropriate temperatures and then were allowed to warm to room temperature. The mixtures were stirred overnight then filtered via syringe or glass fritted filter funnel. The products were analyzed by NMR, AA and Mohr titration for bromide. Concentration, yield and composition were determined by combining the AA and Mohr titration data with NMR data and are shown in Table 2.

EXAMPLE III

PREPARATION OF METHYL(2-THIENYL) CuLi AT LOW TEMPERATURE (Exp. 6468 )

CuBr.Me$_2$S (10.572 g) was weighed into a 3 neck round bottom flask and cooled to $-78°$ C. on a dry ice isopropanol bath. A room temperature solution of 2-thienyllithium [42.0 g (0.0552 moles) in THF/toluene] was added slowly to the dry CuBr Me$_2$S (Me$_2$S=dimethylsulfide) so as not to allow the mixture to warm significantly. Formation of a light yellow solid (2-thienylcopper) appeared complete after 15 minutes, but the mixture was stirred at $-78°$ C. for one hour. Methyllithium [29.93 g (0.0523 moles) in THF/toluene] was then added slowly to this mixture and the precipitate gradually dissolved to form a clear brown solution. The mixture was stirred for three hours at $-78°$ C. then allowed to warm to room temperature overnight with stirring.

While warming, a black precipitate formed (determined to be LiBr by AA and Mohr titration method). Twenty hours post reaction, the stirring was stopped and the cuprate decanted from the solid via syringe. A small amount of precipitate remained suspended and was removed by syringe filtration on bottling. The product composition was determined by NMR:

0.58N in active Me—, 96% yield
Me$^-$ (2-thienyl) : THF : toluene : hexane : Me$_2$S = 1 :1:2.9:10:1.4:1;

on standing overnight, more black precipitate came out of solution and the color changed from gold-tan. The liquid was decanted by syringe from the precipitate and bottled. The product composition was:

NMR analysis: 0.53N in active Me$^{-Me}$-(2-thienyl):THF:toluene:hexane:-Me$_2$S=1:1.1:3.5:11.6:1.2:1.1, Atomic absorption and titration for bromide: Cu:-Li:Br = 1:0.70:0.34.

EXAMPLE IV

PREPARATION OF METHYL(2-THIENYL)CuLi AT LOW TEMPERATURE (EXP. NO. 6414)

Tetrahydrofuran (50 ml) and CuBr Me$_2$S (20.5 g, 0.0997 moles) was mixed in a 250 ml round bottom flask and cooled to $-78°$ C. in a dry ice/isopropanol bath. Methyllithium was added dropwise over 45 minutes to the stirred slurry causing a light yellow precipitate (methylcopper) to form. After MeLi was added (58.82 g in THF/toluene, 0.100 moles) the flask was removed from the bath and allowed to warm above the bath for 10 minutes. During this time the mass turned orange and then back to yellow concurrent with the formation of more light yellow precipitate. The mixture was cooled again and allowed to settle. The supernatant was decanted and the solid washed two times with THF, then with cyclohexane. (THF, at room temperature, was added slowly to precipitate, cooled to $-78°$ C.) for each wash, the precipitate was allowed to settle from the solution and the supernatent was removed by syringe. Ten to fifteen percent (10–15%) of the methylcopper was lost because the precipitate did not settle completely. The methylcopper slurry was cooled to $-78°$ C. and 9.82 g THF and 6.87 g toluene added. Thienyllithium (63.87 g (0.085 moles) in THF/toluene) was added dropwise to the slurry over 20 minutes. The mixture was stirred for 1½ hours at $-78°$ C. During which time the methylcopper gradually dissolved forming a cloudy tan solution. On standing and warming to 0° C., the solution separated into two layers. The upper layer was clear and colorless, and contained no active Me$^-$. The lower layer was dark composition (NMR):

Me$^-$: (2-thienyl):THF:toluene:hexanes:-Me$_2$S = 1:1.3:6.5:1.7:0.83:0.19;

the upper layer was removed and the lower layer cooled to $-78°$ C. 43.2 g toluene was added to the lower layer and then warmed to room temperature. This mixture also separated into two layers. The lower layer was dark brown 0.7 m (NMR) in active Me$^-$, and had the following composition:

NMR:Me$^-$: (2-thienyl):THF:toluene:hexanes: Me$_2$S = 1:1.1:6.1:6.5:0.75:0.17;

Atomic absorption and bromide titration: Cu:-Li:Br = 1:1.4:0:0.84;

the yield was not determined due to the number of NMR samples removed from the reaction mixtures. It was estimated to be 80–90% of Me(2-thienyl)CuLi.

One of the NMR samples of the reaction mixture was sealed and the thermal stability at room temperature was determined by successive NMR spectra of the same sample. A 10 ml sample of the product was also stored for 2½ months. Results of stability studies are in Table I. The cuprate is stable enough to work with at room temperature, but reacts quickly with air to form a bright orange solid which decomposes within a few minutes to form a brown residue.

EXAMPLE V

PREPARATION OF METHYL(BENZOTHIAZOYL)CuLi (EXP. NO. 6418)

Benzothiazole [2.349 g(16.41 mmoles)] was metalated with n-butyllithium [1.207(17.9 mmoles) 90% in isopentane] in hexanes. Benzothiazoyllithium is unstable at temperatures above $-30°$ C. The butyllithium and THF was stirred and cooled to $-78°$ C. in a dry ice/isopropanol bath. The benzothiazole was added dropwise over 10 minutes. First the solution turned dark, then red. After 40 minutes, a dark red precipitate formed. Two hours after addition of benzothiazole, CuBr.Me$_2$S [3.374 g(16.41 mmoles)] was added all at once to the reaction mixture causing it to darken. A yellow precipitate (benzothiazoylcopper) gradually formed over one hour. The mixture was warmed to 0° C. and more precipitate formed. After formation of the precipitate was complete, the stirring was stopped and the mixture was allowed to settle. The supernatent, containing unreacted benzothiazole and dimethyl sulfide, was removed. The yield for the first step was calculated from the excess benzothiazole (74%) in the supernatent. The precipitate was washed three times with cold THF. NMR spectra of the washes indicated that there was no benzothiazoylcopper in the washes.

The slurry was stirred and cooled again to $-78°$ C. and methyllithium [7.75 g(32.0 mmoles) in THF/toluene] added dropwise. The reaction mixture was stirred for 30 minutes at $-78°$ C. forming a dark caramel brown solution of Me(2-benzothiazoyl)CuLi.

Composition:
0.56n in in Me$^-$ (NMR);
Ratios: Me$^-$: (benzothiazoyl):THF:toluene:-Me$_2$S = 1:1.1:9.2:5: trace. One of the NMR samples of the reaction mixture was sealed with tape and the thermal stability at room temperature determined by successive NMR spectra of the same sample. Results of the stability studies are included Table 1.

EXAMPLE VI

COMPARISON OF THE REACTION OF Me$_2$CuLi AND Me(2-THIENYL)CuLi WITH 2-CYCLOHEXENE-1-ONE (EXP. #6471 AND #6465)

Me(2-thienyl)CuLi (1.789 mmole) was placed in a 25 ml round bottom flask, stirred and cooled to $-60°$ C. The substrate solution, containing 40% 2-cyclohexenone, toluene and n-nonane as an internal standard (1.55 mmole 2-cyclohexenone) was added to the stirring cuprate. The reaction mixture was allowed to warm to 0° C. gradually over 30 minutes, then cooled to $-78°$ C. at 30 minutes for quenching with an aqueous solution of NH$_4$Cl/NH$_4$OH. The yield was determined by GC by comparison to nonane.

Me$_2$CuLi (1.94 mmole) was prepared by addition of 3.88 mmoles of methyllithium in THF/toluene to a slurry of CuBr.Me$_2$S in THF at $-78°$ C. The cuprate formed a clear gold to tan solution. 1.90 mmole of 2-cyclohexenone which contained nonane as an internal standard was added to the cuprate and this reaction mixture was stirred for 30 minutes at $-78°$ C. The reaction was quenched at $-78°$ C. with an aqueous solution of NH$_4$Cl/NH$_4$OH, the yield was determined by GC by comparison to nonane.

Yield using Me(2-thienyl)CuLi: 99–100%;
Yield using Me$_2$CuLi: 93–100%.

COMPARISON EXAMPLE

PREPARATION OF Me[N(i-Pr)$_2$]CuLi (EXP. No. 6389)

CuBr.Me$_2$S [1.69 g(8.22 mmoles)] was weighed into a reaction flask and mixed with THF. The slurry was cooled to −78° C. on a dry ice/isopropanol bath. MeLi [5.31 g(9.03 mmoles) in THF/toluene] was added dropwise over 10 minutes causing the formation of a light yelow solid (methylcopper). The mixture was stirred for 20 minutes, in which time it became thick with precipitate.

Lithium diisopropylamide [3.75 g(8.61 mmoles) in THF/toluene] was added dropwise over 10 minutes. Gradually, over one-half hour, the precipitate dissolved forming a clear, tan solution.

The cuprate solution was stored overnight at −60° C., but decomposed quickly when warmed to room temperature. This was determined by successive NMR spectra of samples removed from the reaction mixture.

The cuprate was quenched with benzoyl chloride and the yield of active Me⁻ was determined by GC.

Analysis: Yield: 62% (NMR) 47% (GC) of Me[N-(iPr)$_2$]CuLi Concentration: 0.4N in Me⁻,

EXAMPLE VII

REACTIONS OF METHYL(2-THIENYL)CuLi WITH THREE ALPHA, BETA-UNSATURATED KETONES

The preparation and reactivity of Me(2-thienyl)CuLi had been studied earlier by Nilsson[1] in a different solvent system. Solutions of this complex in diethyl ether were found to be unreactive in affecting 1,4 addition to 2.cyclohexenone, a reactive substrate. However, as mentioned previously in this application, the new composition reported here reacted quantitatively with 2-cyclohexenone at −78° C. to produce the 1,4 adduct in high yields (97%). No 1,2 adduct was detected in the reaction mixture.

[1] (a) Lindstedt, E.; Nilsson, M.; Acta/Chemica Scandinavica B, 40, 466, (1986). (b) Lindstedt, E.; Nilsson, M.; Olsson, T. J., J. Organometallic Chem., 334, 255 (1987).

Further utility studies were carried out in order to study the reactivity of this new composition in affecting 1,4 addition to alpha,beta-unsaturated ketones. The reactions with 2-cyclohexenone, reported above in this application were repeated. In addition, two other enones were chosen which are known to be less reactive toward 1,4 addition. The three enones studied exhibited a wide range of reactivities toward 1,4 addition. 2-Cyclohexenone (1) was the most reactive of the three, then isophorone (2), and then 4, 4a, 5, 6, 7, 8-hexahydro-4a-methyl-2(3H)-naphthalenone (3). Substrates (2) and (3) are less reactive due to steric hindrance at the beta carbon.

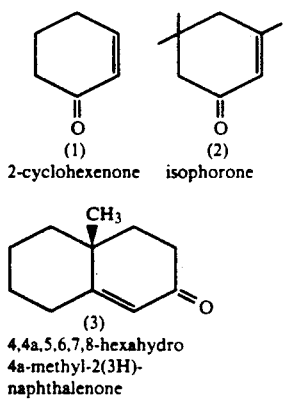

(1) 2-cyclohexenone  (2) isophorone (3) 4,4a,5,6,7,8-hexahydro 4a-methyl-2(3H)-naphthalenone The reactivity of methyl thienylcuprate in affecting 1,4 addition is compared to dimethylcuprate in Table 3. The methyl thienylcuprate in THF/toluene had nearly the same reactivity towards 1,4 addition to 2-cyclohexenone as Me$_2$CuLi. The reaction produced high yields and no 1,2 adduct was detected. 1,4 Addition yields to isophorone (2) were similar for either reagent (89% for cases slightly more 1,2 adduct was formed (1.4% for Methyl(2-thienyl)CuLi vs. <1% for Me$_2$CuLi). In the case of octalone (3), the difference in 1,4 addition yields were somewhat greater. Methyl thienylcuprate gave 60% 1,4 and 15% 1,2 while dimethylcuprate gave 80-90% 1,4 and 10% 1,2 addition. In all three cases, the methyl thienylcuprate produced high yields and required less active methyl than the corresponding reaction with Me$_2$CuLi.

Reaction temperatures were varied from −78° C. to room temperature for reactions with 2-cyclohexenone and isophorone. At −78° C., the cuprate reacted quantitatively with 2-cyclohexenone, but if the reaction was carried out at higher temperatures, yields decreased significantly (to a minimum of 32% at room temperature), even though the substrate was completely consumed. No other major products were identified by GC analysis except for an oily residue which collected on the injector (injector temperature: 300° C.). If excess substrate was used (cuprate:substrate=0.88:1), the substrate was still completely consumed. This is likely due to reaction of the enolate intermediate formed in 1,4 addition with the substrate.

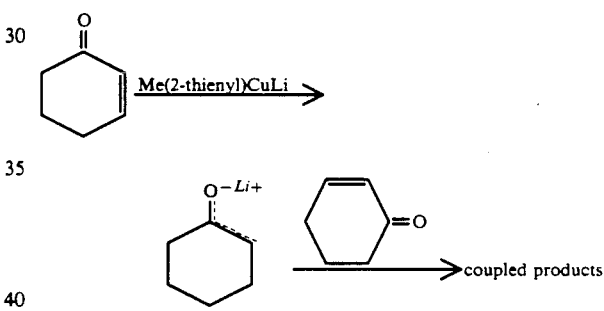

Isophorone did not react with the methyl thienylcuprate at −78° C. Instead, the solution formed a deep orange color, which persisted 2½ hours until the solution was quenched. However, if the temperature was increased, 1,4 addition occurred. Yields for 1,4 addition increased as the temperature of the reaction was increased from −78° to 0° C. and reached a maximum at 0° C. (yield: 89%). Yields decreased slightly to 84% when the reaction was carried out at room temperature.

In summary, the reactivity of this reagent is similar to Me$_2$CuLi, but has several advantages over Me$_2$CuLi due to its thermal stability and solubility. Since the reagent is prepared in advance and can be stored, low temperature formation of the cuprate in situ is avoided. Since it is thermally stable and soluble, a wider range of reaction temperatures are available for synthetic reactions. The actual temperature chosen will depend on the substrate and the reactivity of the substrate at different temperatures.

Experimental Procedure

Reactions of Methyl Thienylcuprate with Enones. The methyl thienylcuprate solution (2–3 g, 1–2 mmole), prepared according to Example 1, was transferred via syringe techniques into a small flask or test tube, magnetically stirred, and cooled to the appropriate temperature. The substrate solution, containing toluene, 15–40% cyclohexenone or isophorone and an internal standard was then added via syringe techniques. No additional solvent was necessary in reactions with the methyl thienylcuprate. For reactions with 2-cyclohexenone and isophorone, temperatures were varied between −78° C. and room temperature, and reaction times were varied between 5 minutes and 2½ hours to determine the best reaction conditions. The reactions were quenched with a degassed, aqueous solution of NH₄Cl (3M). The mixture was extracted with ethyl ether and the organic phase analyzed by GS was described in the analytical section below. Retention times and response factors for the 1,4 addition products were determined by comparison to actual samples purchased from Aldrich Chemical Company.

Reactions of Methyllithium with Enones. Methyllithium in THF/toluene was reacted with 2-cyclohexenone and isophorone for comparison and to determine the retention times for the 1,2 adducts. The same procedure was used as for the methyl thienylcuprate except that the reactions were run at −78° C. for 2-cyclohexenone and from −40 to −20° C. for isophorone.

Reactions of Lithium Dimethylcuorate with Enones. Lithium dimethylcuprate was prepared by a modification of a literature procedure[2]. CuBr.Me₂S (0.398 g, 1.94 mmole) was weighed into a 25 ml three neck round bottom flask. The solid was purged with argon for 20 minutes. Tetrahydrofuran (5 ml) was added to the solid and the slurry was stirred and cooled to −78° C. in a dry iceisopropanol bath. Adding MeLi in THF/toluene (1.11 g of 2.0M solution, 1.94 mmole) to the stirring slurry causing the formation of a yellow precipitate. The mixture was removed from the low temperature bath and allowed to warm and more yellow precipitate formed. Temperatures were not allowed to exceed 0° C. Then the mixture was cooled again to −78° C. in the bath, and an additional 1.11 g (1.94 mmole) MeLi was added. The solid dissolved, forming a clear solution, the color of which varied from almost colorless to gold-brown. The 1,4 addition reaction was run immediately to avoid decomposition of Me₂CuLi. A substrate solution containing toluene, 15–40 wt. % 2-cyclohexenone or isophorone, and an internal standard was added to the cuprate solution. The reaction mixture was quenched with a degassed, aqueous solution of NH4Cl (3M), and analyzed by GC as described in the analytical section.
[2] Posner, G. H.; Organic Synthesis, 19, 59, (1972).

Analytical Procedures. The composition of cuprate solutions were determined by a combination of NMR spectra, atomic absorption for copper and lithium and potentiometric titration for bromide. NMR spectra were obtained on a Varian EM-360L 60 mHz NMR spectrometer or a General Electric QE-300 300 mHz NMR. Lithium and copper content were determined by atomic absorption spectroscopy of quenched solutions, after the samples were acidified and the organic components removed by evaporation. Samples were treated similarly for bromide analysis, then neutralized, and bromide content was determined by potentiometric titration. Gas chromatograms were obtained on a Varian 3300 GC with a 5 micron thick Altech RSL160 polydimethylsiloxane column. Chromatograms were obtained at 130° C. with a 3.3 ml/minute helium flow rate. Yields were determined by comparison to an internal standard (nonane or decane). Retention times for reactants and 1,4 addition products were determined by comparison to authentic samples purchased from Aldrich. Retention times for 1,2 addition products were determined by analysis of the reaction mixture after reaction of the enones with MeLi in THF/toluene.

Example VIII

Thermal Stability of Methyl Thienyl Cuprate

The thermal stability at 40° C. was determined for the methyl thienyl cuprate in THF/toluene. This experiment was done to simulate storage and shipping of this product in the summer months.

A new procedure was developed in which the samples remained sealed in NMR sample tubes for the duration of the test. Three NMR samples of the cuprate (0.6M) were stored in a dry, argon purged jar which was submerged in a 40° C. oil for 29 days. Every 7 days the jar was removed from the bath, equilibrated to room temperature, and flushed with argon. The NMR spectra were obtained on the samples. Weight per cent values for all organic components were determined by combination of NMR and initial values for Cu, Li and Br content as described in the analytical section of Example Seven. The results of the stability test show that the average loss of active methyl group was 0.86%/day. This compares favorably to thermal stabilities at 40° C. of other ortholithium/THF compositions:

| | |
|---|---|
| Lithco MeLi in THF/toluene | 1.19%/day |
| Lithco MeLi 9307 (MeLi in THF/cumene with 3–7% magnesium) | 0.016%/day |
| Lithco LDA 9505 (Lithium diisoproplamide in THF/hydrocarbon with 5% magnesium) | 0.48%/day |

The rate of decomposition varied over the 29 day test, being the greatest during the second and third weeks, then leveling off during the fourth week. Thienyl. and THF content also decreased, but the rate of loss was much slower than that for Methyl-. The solutions did not generate gas pressure. This indicates that the decomposition reaction probably does not produce methane gas.

EXAMPLE IX

PREPARATION AND THERMAL STABILITY OF VARIOUS THIENYL CURPRATE COMPOSITIONS:

This example describes the effect of composition on the preparation and stability of cuprates containing the thienyl⁻ stabilizing ligand. Stable cuprates in limited tetrahydrofuran (THF) can be prepared utilizing other transferrable groups besides methyl⁻. Examples include: methyl⁻, ethyl⁻, butyl⁻, and phenyl⁻ THF content was varied from 0.62 to 21.5 moles per mole of transferrable R group ($R_T$). The magnesium content of a starting material ($R_T$Li) was varied from 0 to 100%. Also, four different solubilizing hydrocarbon solvents were evaluated.

The different compositions of thienyl cuprates were prepared by a method similar to that employed to prepare Methyl 2-thienyl)CuLi as described in Examples I-III herein. The preparation and stability tests are described in the experimental section below. The results of the experiments are shown in Table IV. These results demonstrate several points:

1. Thienyl cuprate compositions can be prepared utilizing various transferrable groups which are several times more stable than any alkyl cuprate described in the literature. For example, methyl and butyl thienyl cuprates showed decomposition rates of nearly 0% methyl per day and 3.9% butyl- per day (numbers 1, 2, and 8, Table IV). All of the literature references on cuprate stability described cuprate compositions which were stable less than 2 days and which were unsuitable for a commercially viable product. A tert-butylphosphido-(alkyl)cuprate was described as being "extremely stable" even though it decomposed approximately 15% in 24 hours (Martin, S. F.; Fishpaugh, R. R.; Power, J. M.; Giolando, D. M.; Jones R. A.; Nunn, C. M.; Cowley, A. H., J. Am. Chem. Soc., 110 p. 7228 (1988)). One cuprate which was stable contained no transferrable group ($R_T$), and was intended for use only as a precursor for preparing alkyl cuprates at low ($-78°$ C.) temperatures. The cuprate composition formed in this manner had to be used immediately due to its extreme instability (Lipshutz, B. H.; Koerner, M.; Parker, D. A., Tetrahedron Letters, 28(9), pp. 945-8, (1987)). The cuprates described in the examples herein are not precursors; they are ready to use in organic reactions without the addition of other reagents. Bertz systematically studied the thermal stability of a series of reactive alkyl heterocuprates which had improved stability over dialkylcuprates (Bertz, S. H.; Dabbagh, G., J. Chem. Soc., Chem. Commun., p. 1030, (1983), and Bertz, S. H.; Dabbagh, G.; J. Org. Chem., 49 p. 1119, (1984)). None of the cuprates studied by Bertz or cited in these two publications were as stable as the cuprates in THF/aromatic or saturated hydrocarbon solvent described herein.

2. Thienyl cuprates in limited THF solutions are significantly more stable than the same cuprates in pure THF. For example, Methyl(2-thienyl)CuLi solutions decomposed at a rate of nearly 0% per day in limited THF, while solutions in pure THF decomposed at a rate of 7.3% per day (numbers 1, 2, and 7, Table IV). Bu(2-thienyl)CuLi solutions decomposed at a rate of 3.9% per day in limited THF/cyclohexane, while solutions in pure THF decomposed at a rate of 45% per day (numbers 8 and 12, Table IV). This demonstrates the stabilizing effect of limited Lewis base solutions over solutions in which the entire solvent is Lewis base (i.e. THF or diethyl ether). No literature references exist to this date which describe the preparation of cuprate solutions in limited Lewis base plus aromatic or saturated hydrocarbons.

3. Magnesium content of the starting materials equal to or less than 11.4% (11.4% = (moles magnesium/(total moles of magnesium+lithium))×100), does not adversely affect the preparation or apparent stability of the cuprate. Magnesium content higher than 50% in the starting materials resulted in low levels of copper in the product and incomplete formation of the cuprate. (See numbers 3 through 6 in Table IV.)

The magnesium content of the starting materials is important because some methyllithium products contain 3 to 7 mole % magnesium in the form of dimethylmagnesium. The magnesium acts as a stabilizing agent, so that the product can be stored without precipitation or significant decomposition.

4. The type of hydrocarbon solvent affects the stability of the cuprate, though this effect is not as great as the amount of THF. For example Bu(2- (thienyl)CuLi is 1 to 2% per day more stable in THF/cyclohexane than in THF/toluene (numbers 8, 10, and 11, Table IV).

Experimental Procedure:

Thienyl cuprates were prepared by a method similar to and using the same type equipment as described in Examples I-III herein. The cuprates were analyzed by nuclear magnetic resonance (NMR), ion coupled plasma (ICP), and potentiometric titration for halide. The experimental methods and results are described below.

The cuprates were prepared by either Method A or Method B described below, the choice of method depending on physical state of $R_T$Li and practical considerations for handling the reactive solids. The amount of reagents ($R_T$Li, thienyllithium and CuBr.Me$_2$S) were such that the molar ratios between the three was approximate 1. A small stoichiometric excess of CuBr.Me$_2$S and thienyllithium was used to assure the final product contained sufficiently high Cu$^+$ and Thienyl$^-$ contents. The appropriate solvent was added to the reaction in an amount sufficient to obtain a final normality of $R_T$ of 0.1 to 0.7N.

Methyllithium in THF/toluene, methyllithium in THF/cumene with magnesium, dimethyl magnesium in THF/toluene and THF/cumene, ethyllithium in THF/cyclohexane, pure ethyllithium solid, butyllithium in hexane, concentrated butyllithium in hexane, and phenyllithium in cyclohexane were obtained from Lithium Corporation of America (Lithco). Thienyllithium was prepared from thiophene, butyllithium in hexanes and THF, by the following method: 1 mole of thienyllithium and 1.2 mole of THF were mixed in a dry, argon purged round bottom three neck flask. The solution was stirred, cooled to $-20°$ C. and then 0.95 mole butyllithium (17-25 wt % in hexane) was added drop wise over 45 minutes to 1 hour. The reaction temperature was maintained at $-20°$ C. for 2-3 hours, then allowed to warm to room temperature overnight. The reaction mixture was stirred constantly during the reaction. The product, a 1:1 complex of thienyllithium and THF was filtered and stored in a glass bottle equipped with a ground glass joint. Solid phenyllithium was prepared by concentration of Lithco's phenyllithium product in hexanes, and collection of the solid by filtration. An argon atmosphere was maintained over all organolithium solids and solution during all procedures. All glassware was thoroughly cleaned, baked at 150° C. overnight, then purged cool with argon before use.

Preparation Method A:

An admixture or solution was prepared containing $R_T$Li/($R_T$)$_2$Mg($R_T$=methyl$^-$, butyl$^-$, ethyl$^-$) solutions and thienyllithium THF solid. This was added to a slurry of CuBr. Me$_2$S in the appropriate solvent (toluene, cumene, hexane, cyclohexane, or tetrahydrofuran) at a temperature of $-60°$ to 25° C. A small amount of dry solvent was used to wash any remaining organolithium into the CuBr.Me$_2$S. The reaction mixture was maintained within the temperature range of $-60°$ to 25° C. for at least 30 minutes, then allowed to equilibrate to room temperature. The stirring was stopped and the solid formed in the reaction was allowed to settle to the bottom of the flask. The supernatant which contained the cuprate product was decanted for analysis and stability tests.

Preparation Method B:

Solid $R_T$ ($R_T$=methyl$^-$, or phenyl$^-$) and solid thienyllithium tetrahydrofuran were mixed and the appropriate solvent was added to this solid mixture. Tetrahydrofuran (THF) was added at $-78°$ C. while other solvents (toluene, cumene, cyclohexane) were added at a temperature within the range $-20°$ to 25° C. The temperature was not allowed to fall below the freezing point of the solvent. The slurry or solution of organolithium and solvent was stirred and then CuBr.Me$_2$S was added either as a solid or with a small amount of solvent. The mixture was stirred and the temperature maintained at −78° C. for THF solutions, or within the range of −10° to 20° C. for other solvent systems, for at least 30 minutes, then allowed to equilibrate to room temperature. The stirring was stopped and the solid formed in the reaction was allowed to settle to the bottom of the flask. The supernatant which contained the cuprate product was decanted for analysis and stability tests.

Method to Determine Thermal Stability:

The thermal stability of the cuprate solutions were determined by successive NMR spectral analysis of samples stored in NMR tubes. The NMR tubes were baked in an oven at 150° C. overnight, then purged with argon until cool. Samples of the supernatants from the preparations described above were transferred to the NMR tubes and the tubes were sealed with teflon caps. An argon atmosphere was maintained over the solutions during sample preparation to minimize the effect of oxidative decomposition. To assure that air did not leak into the sample tubes after they were capped, the entire sample tube was sealed in a jar which had been baked overnight at 150° and purged with argon until cool. An argon atmosphere was maintained inside the jar.

Samples were removed from the jar, analyzed by NMR then replaced. Thermal stability at room temperature was determined as the loss in active $R_T^-$ determined from the NMR integration. The test was terminated before 30% of the active $R_T^-$ was lost through decomposition. As a control, a sample of Lithco's methyllithium 9307 (methyllithium in THF/cumene with 7 mole % Me$_2$Mg), which is known to be stable at room temperature was stored in NMR tubes in the same manner. There was no significant change in the NMR of spectra of methyllithium after storing in this manner for 2 months. Experimental details and data from samples prepared by either Method A or Method B and tested for thermal stability are reported in Table IV.

Example X

PREPARATION OF $R_T$(R-THIENYL)CuLi FROM COPPER(I) HALIDES

A new synthetic process was developed in order to avoid the use of CuBr.Me$_2$S in the preparation of $R_T$(2-thienyl)CuLi. The new process uses CuCl, CuBr, or CuI, which are several times less expensive than CuBr-.Me$_2$S and more readily available in large quantities for plant production. The particular CuBr used for this example is less pure than halide salts commonly used for cuprate preparations. It is the least expensive of the three halides and is routinely stored in the air. This new process also allows one to change the amount and type of halide present in the final cuprate product. The presence of different halides can alter the stereo-selectivity and regioselectivity of the reagent in some organic reactions. Also, the type and amount of halide slats affect waste disposal procedures.

Copper(I) bromide, copper(I) chloride, and copper(I) iodide were not reactive enough when substituted for CuBr.Me$_2$S in the processes described in patent examples I-III. The solution formed contained low values of Cu$^+$ compared to other components of the cuprate ($R_T^-$, thienyl$^-$, and Li$^+$), which would make the reagent less reactive and regioselective in organic reactions. Particularly, reactions such as 1,4 addition of $R_T^-$ to alpha,beta-unsaturated ketones would give competing 1,2 addition products as well as 1,4 addition products.

However, these three halides can be used to produce $R_T$(2-thienyl)CuLi if the salt is first conditioned with 1-5 mole % $R_T$ (based on total copper: moles of conditioner=(0.01 to 0.05) X moles of copper), then solvated with approximately 1 mole Me$_2$S. $R_T$ anion groups which have been used are Lithco's methyllithium in THF/toluene or in THF/cumene with 0 to 4 mole % magnesium and Lithco's butyllithium. Experiments were carried out to compare the products obtained with these salts using different methods of preparation and the results are shown in Table V below. A preparation using CuBr.Me$_2$S is included for comparison (Number 8).

As shown in Table V, conditioning and solvation with dimethyl sulfide of CuBr, CuCl, and CuI produced a product with much higher copper content than in preparations where these two procedures were omitted. Copper content in the product increased over ten times in the case of CuCl, four times in the case of CuI and two times in the case of CuBr. If the salt was solvated but not conditioned, much lower yields were obtained. CuBr. Me$_2$S does not require solvation or conditioning (Number 8, Table V). Even if the dimethylsulfide is removed from the salt by heating under a stream of argon, the remaining CuBr is reactive enough that conditioning or solvation with additional Me$_2$S is unnecessary.

This process can be used for other transferrable groups. Butyl(2-thienyl)CuLi was prepared in a similar manner with good results as shown in number 9 in Table V.

In summary, this new process provides: 1) A way to prepare stable cuprate compositions using less expensive starting materials. 2) A way to prepare the same compositions with differing amounts of lithium halide present. 3) A method which can be applied to other $R_T^-$ and $R_R^-$. 4) A simple process which produces good results at room temperature.

Experimental Procedure:

The same procedure was followed with each halide starting with commercially available copper bromide, copper chloride, and copper iodide. (CuBr 98% pure, CuCl 99.+ % pure, CuI 99.+ % pure.) All salts were stored and transferred under an atmosphere of argon. The copper salt was weighed into a round bottom flask equipped with a magnetic stirrer and dried toluene was added. A few drops of Lithco's methyllithium in THF/toluene was added, equal to an amount of 0.01 to 0.05 moles of methyllithium per mole of copper salt. The salt was allowed to condition with stirring for 30 minutes. Then liquid dimethyl sulfide was added, an amount approximately equal to one mole per mole of copper salt. This was allowed to stir for 10 to 15 minutes more, then a solution or admixture of methyllithium and thienyllithium was added to the slurry in the manner described in patent Examples I-III. The reaction was cooled in a dry ice hexane bath of sufficiently low temperature to keep the reacting slurry at 25° C. or below. After this point, the preparation was essentially the same as described in Example IX above.

The supernatant was removed by syringe and analyzed by proton nuclear magnetic resonance (NMR), ion coupled plasma (ICP), and potentiometric titration for halide. The solutions are apparently stable, samples removed one day later had essentially the same analysis. Experimental details and data for 9 examples are reported in Table V.

The foregoing examples show that liquid aliphatic and cycloaliphatic hydrocarbons are useful in practicing this invention. Preferred aliphatics include, but are not limited to $C_5$ to $C_{19}$ paraffins and cycloparaffins.

The examples have also shown that copper (I) salts are preferably treated with a solvating agent before being introduced into the reaction. Solvating agents include, but are not limited to sulfur containing alkyls such as dimethylsulfide and dimethyldisulfide and the like.

Preferred $R_T$ groups include, but are not limited to methyl, ethyl, n-propyl, isopropyl, secondary butyl, isobutyl, tertiary butyl, 2-ethylhexyl and n-octyl.

EXAMPLE XI

A cuprate of the formula:

is prepared wherein $R_R$ is a nontransferable group which stabilizes the cuprate. This reagent has utility in organic synthesis because $R_T Li$ can be added to it to form a higher order cuprate:

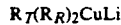

which is reactive and useful for transfer of $R_T$ to a substrate. The cuprate wherein $R_R$ is the 2-thienyl group is prepared in the following manner.

Thienyllithium. tetrahydrofuran etherate is mixed with additional tetrahydrofuran and toluene to form a 1.3M solution. The ratio of tetrahydrofuran/2-thienyl is 1.5. Copper bromide (0.5 mole), is stirred with toluene and methyllithium (0.005 mole). The methyllithium acts as a conditioner and is consumed by impurities in the toluene and copper bromide. After conditioning 2 hours, 0.5 moles of dimethyl sulfide is added to the slurry. The slurry is cooled to $-30°$ C. and the thienyllithium solution is added to the stirring copper bromide slurry. The ratio of reactants is two moles of thienyllithium per mole of copper bromide. The reaction is stirred and allowed to warm to room temperature. The resulting mixture is filtered and the supernatent bottled.

The utility of this reagent is demonstrated by adding a $R_T Li$, such as $Me_3SiCCCH_2Li$ (prepared by addition of butyllithium to $Me_3SiCCCH_3$) to the (2-thienyl)-2CuLi in a 1:1 stoichiometric ratio at low temperatures to form the higher order cuprate. The higher order cuprate can be used immediately for addition of $R_T$ in epoxide openings.

TABLE I

Thermal Decomposition of Cuprates at Room Temperature

| Exp. # | Cuprate | Solvent | Stability |
|---|---|---|---|
| 6387 | $Me[N(iPr)_2]CuLi$ | THF | Unstable |
| 6389 | $Me[N(iPr)_2]CuLi$ | THF/cyclo | Unstable |
| 6403 | $Me[N(iPr)_2]CuLi$ | THF/tol | 13% decomp. in 45 min. |
| 6402b | $Me[N(iPr)_2]CuLi$ | THF/hex | Unstable |
| 6418 | Me(2-benzothiazoyl)CuLi | THF/tol/hex | 5% decomp./day after 4 days |
| 6414 | Me(2-thienyl)CuLi (Method A) | THF/tol/hex | a. 0.81% decomp./day after 12 days in NMR tube b. no decomp. after 2¼ months in sealed glass bottle |
| 6496 | Me(2-thienyl)CuLi | THF/tol | no decomp. after 18 days |
| — | $Bu_2CuLi$* | $Et_2O$ | 18% decomp. in 30 min. |
| — | $Bu[(iPr)_2]CuLi$* | $Et_2O$ | 3% decomp. in 30 min. |

*From Bertz, S. H.; Dabbagh, G.; J. Chem. Soc., Chem. Commun., 1030, (1982); Bertz, S. H.; Dabbagh, G.; Villacorta, G. M., J. Am. Chem. Soc., 104, 5824, (1982).

TABLE II

PREPARATION OF Me(2-THIENY)CuLi AT VARIOUS TEMPERATURES

| Exp. # | Temp., C. | Conc. Me—(N) | Yield (Me—) | Composition (Ratio to Me—) Me—:Th—:THF:Tol:Hexanes:Me$_2$S= |
|---|---|---|---|---|
| 6474a | 25-33 | 0.54 | 80% | 1:1.02:3.35:11.7:0.93:0.90 |
| 6482a | 25-33 | 0.54 | 80% | 1:1.10:3.71:12.4:0.17:0.20 |
| 8482b | 25-33 | 0.55 | 82% | 1:1.08:3.65:11.8:0.37:0.64 |
| 6474b | 0 | 0.50 | 72% | 1:1.11:3.69:13.0:0.81:0.98 |
| 6474c | −15 | 0.49 | 73% | 1:1.09:3.64:13.3:0.86:1.10 |
| 6474d | −50 | 0.54 | 72% | 1:1.14:3.72:12.3:0.09:0 |
| 6482c | −50 | 0.34 | 56% | 1:1.60:5.28:20.0:1.00:1.60 |
| 6482d | −60 | 0.44 | 75% | 1:1.39:3.99:14.8:0.73:1.07 |
| 6487 | 25-33 | 0.48 | 84% | 1:1.08:3.08:14.3:0.73:1.14 |
| 6495 | 25-30 | 0.39 | (74%)[4] | 1:2.06:5.01:17.9:0.44:1 |
| 6496 | 25-30 | 0.44N | 69% | 1:1.46:3.76:15.2:0.60:1.18 |
| 6515[5] | 30-45[6] | 1.15 | 85.7% | 1:1.10:2.53:3.93:0.175:1.05 |

(1) Yields were determined from NMR spectra obtained before and after addition of the MeLi/ThLi solution to the CuBrMe$_2$S. Yields were calculated by comparison of Me— and THF peaks.

(2) The temperature of the reaction mixture was 5 C. higher than room temperature due to heat generated by the stirring plate.

(3) Composition determined by NMR.

(4) Beginning THF content not available due to suspended ThLi-THF etherate. This value calculated relative to toluene.

(5) Preparation of concentrated cuprate. Same procedure, except that solid ThLi etherate was mixed with 2M MeLi in THF/Toluene before addition to CuBrMe$_2$S.

(6) Temperature returned to 25-30 C. 5-10 minutes after reaction.

TABLE III

1,4 ADDITION OF METHYL THIENYLCUPRATE TO THREE ENONES

| Substrate | (ref) | Reagent | % 1,4 | % 1,2 | % enone Remaining | Me⁻/Substrate, Conditions |
|---|---|---|---|---|---|---|
| (1) 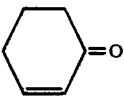 | | Me(2-thienyl)CuLi | 97 | ~0 | ~0 | 1.2, −78 C, 30 min. |
| | | Me₂CuLi | 98 | ~0 | ~0 | 2.1, −78 C, 30 min. |
| (2) 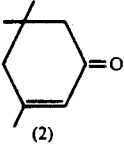 | | Me(2-thienyl)CuLi | 89 | 1.4 | ~0 | 1.4, 0 C, 1¼ hours |
| | | Me₂CuLi | 94 | <1% | 4.4 | 2.4, −40 C to −20 C, 1 hour |
| (3) 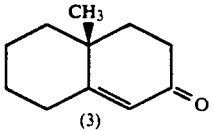 | Bertz* | Me(2-thienyl)CuLi | 60 | 15 | 25 | 1.1, 0 C, 30 min., in ether |
| | Bertz* | | 80–90 | 10 | ~ | 2.2, 0 C, 30 min., in ether |

*Smith, Robert; unpublished results.

TABLE IV

COMPOSITIONS AND ROOM TEMPERATURE STABILITIES OF CUPRATE COMPOSITIONS CONTAINING VARIOUS TRANSFERRABLE GROUPS

| | Compound | Solvent System | Ratio THF:$R_T$ | Stability: % Loss Active $R_T$/Day |
|---|---|---|---|---|
| 1. | Me(2-thienyl)CuLi | THF/toluene | 3.8:1 | ~0%/day |
| 2. | Me(2-thienyl)CuLi | THF/toluene hexane | 6.1:1 | ~0%/day |
| 3. | Me(2-thienyl)CuM M = L + ¼Mg | THF/cumene | 2.6:1 | not available |
| 4. | Me(2-thienyl)CuM M = Li + ¼ Mg | THF/cumene | 3.0:1 | not available |
| 5. | Me(2-thienyl)CuM M = Li + ¼ Mg | THF/toluene | — | — |
| 6. | Me(2-thienyl)CuM M = Li + ¼ Mg | THF/toluene | — | — |
| 7. | Me(2-thienyl)CuLi | THF | 19.3:1 | 7.3%/day |
| 8. | Bu(2-thienyl)CuLi | THF/cyclohexane | 0.95:1 | 3.9%/day |
| 9. | Bu(2-thienyl)CuLi | THF/hexane | 0.62:1 | 4.4%/day |
| 10. | Bu(2-thienyl)CuLi | THF/toluene | 0.94:1 | 5.2%/day |
| 11. | Bu(2-thienyl)CuLi | THF/toluene | 1.5:1 | 8.5%/day |
| 12. | Bu(2-thienyl)CuLi | THF | 21.5:1 | 45%/day |
| 13. | Ph(2-thienyl)CuLi | THF/toluene | 2.1:1 | not available |
| 14. | Et(2-thienyl)CuLi | THF/toluene | 1.46:1 | 8.4%/day |
| 15. | Et(2-thienyl)CuLi | THF | 16.7:1 | >100%/day[b] |
| 16. | Phenyl(2-thienyl)CuLi | THF/cyclo | 2.8:1 | Not available |

| Ion Composition $R_2 = (R_T + R_R)$ | Remarks | Experimental Ref. # |
|---|---|---|
| R₂:Cu:Li:LiBr = 1:.48:.56:.22 | See footnote c. | 6496 |
| R₂:Cu:Li:LiBr = 1:0.62:0.38:0.51 | See footnote d. | 6414 |
| R₂:Cu:Li:LiBr:Mg = 1:.45:.49:.05:.028 | Prepared from Lithco's MeLi in THF/cumene with 4 mole % Mg. See footnotes a & e. | 6609 |
| R₂:Cu:Li:LiBr:Mg = 1:.51:.44:.044:.041 | Prepared from Lithco's MeLi in THF/cumene with 10 mole % Mg. See footnotes a & f. | 6693 |
| R₂:Cu:Li:LiBr:Mg = 1:0.15:0.47:0.22:0.19 | Did not form cuprate. Prepared from 50:50 mixture of Me₂Mg & MeLi. See footnotes a & g. | 6685 |
| R₂:Cu:Li:LiBr:Mg = 1:0.7:~0:0.46:0.45 | Did not form cuprate. Prepared from Me₂Mg. See footnotes a & h. | 6710 |
| R₂:Cu:Li:LiBr = 1:.36:.62:.39 | See footnote i. | 6711 |
| R₂:Cu:Li:LiBr = 1:.46:.54:.02 | See footnote j. | 6692 |
| R₂:Cu:Li:LiBr = 1:.49:.51:.039 | See footnote k. | 6681 |
| R₂:Cu:Li:LiBr = 1:.44:.57:.02 | See footnote l. | 6662 |
| R₂:Cu:Li:LiBr = 1:.42:.58:.01 | See footnote m. | 6664 |
| R₂:Cu:Li:LiBr = 1:.59:.41:.55 | See footnote n. | 6689 |
| R₂:Cu:Li:LiBr = 1:.50:.42:.10 | See footnote o. | 6668 |
| R₂:Cu:Li:LiBr = 1:0.41:0.59:0.036 | See footnote p. | 6703 |
| Not available | See footnote q. | 6716 |
| R₂:Cu:Li:LiBr = | See footnote r. | 6709 |

TABLE V

PREPARATION OF $R_T$(2-thienyl)CuLi FROM VARIOUS COPPER (I) SALTS

| | Cu(I) Salt | Solvating Agent (Ratio) | Conditioning | Yield: Methyl⁻ Group as MeLi or Me(2-thienyl)CuLi | Composition $R_2$:Cu:Li:LiX | Experimental Ref # |
|---|---|---|---|---|---|---|
| 1. | CuBr | None | No | 38% | 1:0.21:0.73:0.30 | 6544 |
| 2. | CuCl | None | No | 73% | 1:0.04:0.99:0.01 | 6436 |
| 3. | CuI | None | No | 84% | 1:0.14:0.86:0.24 | 6712 |
| 4. | CuBr | Me$_2$S (1:1) | Yes | 92% | 1:0.45:0.50:0.07 | 6632 |
| 5. | CuCl | Me$_2$S (1:1) | Yes | 51% | 1:0.44:0.59:0.02 | 6672 |
| 6. | CuI | Me$_2$S (1:1) | Yes | 42% | 1:0.85:0.15:1.6 | 6713 |
| 7. | CuBr | Me$_2$S (1:1) | No | 63% | 1:0.39:0.44:0.28 | 6714 |
| 8. | CuBr.Me$_2$S | No | No | 86% | 1:0.55:0.48:0.13 | 6715 |
| Preparation of Butyl (2-thienyl)CuLi from CuBr: | | | | | | |
| 9. | CuBr | Me$_2$S (1:1) | Yes | Yield of Butyl⁻ 93% | 1:0.44:0.58:0.018 | 6662 |

TABLE IV-continued

1:0.52:0.47:0.19

Footnotes for TABLE IV:
(a) Numbers 2 through 5 were prepared from Lithco methyllithium containing 4. (No. 2), 11.4 (No. 4), and 50 (No. 5) mole % magnesium (mole % Mg = (moles Mg/moles Li + moles Mg)) × 100). Number 6 was prepared from Lithco dimethylmagnesium. Preparations utilizing higher magnesium content (50 and 100%), were not successful.
(b) Product decomposed 29.3% in two hours and 15 minutes. Estimated decomposition rate was 13% per hour.
Details of experimental data:
(c) Compound 1. Prepared using the procedure described in Example 1.
(d) Compound 2. Prepared using the procedure described in Example IV.
(e) Compound 3. Prepared by Method A, except that the R$_T$Li/((R$_T$)$_2$Mg solution was Lithco's methyllithium in THF/cumene containing 4% magnesium (mole % Mg = (moles Mg/(moles Li + moles Mg)) × 100).
(f) Compound 4. Prepared by Method A, except that the R$_T$Li/((R$_T$)$_2$Mg solution was Lithco's methyllithium in THF/cumene containing 11.4% magnesium (mole % Mg = (moles Li + moles Mg)) × 100).
(g) Compound 5. Prepared by Method A, except that the R$_T$Li/((R$_T$)$_2$Mg solution was Lithco's methyllithium in THF/toluene containing 50% magnesium (mole % Mg = (moles Mg/(moles Li + moles Mg)) × 100).
(h) Compound 6. Prepared by Method A, except that the R$_T$Li/((R$_T$)$_2$Mg solution was Lithco's dimethylmagnesium in THF/toluene containing 100% magnesium (mole % Mg = (moles Mg/(moles Li + moles Mg)) × 100), and no lithium.
(i) Compound 7. Prepared by Method B. Solid methyllithium.THF and thienyllithium THF were mixed in a round bottom flask cooled to −78° C. in a dry ice-isopropanol bath. THF was added slowly with stirring at −78°. A slurry of dry CuBr.Me$_2$S and THF was added to the methyllithium/thienyllithium mixture at −78° C. This mixture was stirred for 30 minutes, then samples were removed for stability studies and allowed to equilibrate to room temperature.
(j) Compound 8. Prepared by Method A. Butyllithium in cyclohexane was mixed with thienyllithium.THF solid and this mixture was transferred to a slurry of dry CuBr.Me$_2$S in cyclohexane. The reaction temperature was maintained at a temperature 5-10 degrees above the freezing point of the THF/cyclohexane solvent mixture by use of a dry ice-hexane bath.
(k) Compound 9. Prepared by Method A. Butyllithium in hexanes was mixed with thienyllithium.THF solid and this mixture was transferred to a slurry of dry CuBr.Me$_2$S in hexanes. The reaction temperature was maintained at a temperature 5-10 degrees above the freezing point of the THF/cyclohexane solvent mixture by use of a dry ice-hexane bath.
(l) Compound 10. Prepared by method described in Example X except that Lithco's butyllithium in toluene was used in place of methyllithium in THF/toluene. The conditioner of 0.05 moles butyllithium per mole of CuBr.
(m) Compound 11. Prepared by method described in Example X except that Lithco's butyllithium in toluene was used in place off methyllithium in THF/toluene. The conditioner was 0.05 moles butyllithium per mole of CuBr.
(n) Compound 12. Dry CuBr.Me$_2$S was mixed with THF and cooled to −78° C.. Thienyllithium.THF was added to this slurry and stirred for 30 minutes at this temperature. Lithco's concentrated butyllithium (87.2 wt % butyllithium in hexanes), was then added slowly and the temperature maintained at −78° C.. The cuprate was stirred for 30 minutes at this temperature then a sample removed at −78° C. for stability studies.
(o) Compound 13. Prepared by Method B. Butyllithium was solvent free phenyllithium and the solvent was toluene. One mole of THF was added after the reaction to solubilize the product.
(p) Compound 14. Prepared by Method A, except that the R$_T$Li solution was Lithco's ethyllithium in THF/toluene.
(q) Compound 15. Prepared by Method B, except that thienyllithium.THF solid was added to the CuBr.Me$_2$S in a THF slurry and the temperature of this mixture was maintained at −78° C. in a dry ice-isopropanol bath. A solution of Lithco's ethyllithium in THF/toluene was added slowly to this mixture with stirring. The mixture was stirred, maintaining the temperature at −78° C., then a sample for stability test was removed via syringe.
(r) Compound 16. Prepared by Method A, except that R$_T$Li was Lithco's phenyllithium in cyclohexane. THF was added to the phenyllithium/thienyllithium mixture before reacting with CuBr.Me$_2$S at the amount of a mole of THF per mole of phenyllithium.

We claim:

1. An organometallic composition containing copper(I) comprising an organometallic composition of the general formula $$R_T R_R CuLi$$

wherein $R_T$ is a transferable anionic group, $R_R$ is a residual anionic group and containing:
(a) 0.01 to 1.2 mole equivalents of a halide selected from chloride, bromide or iodide,
(b) 0 to 0.12 mole equivalents magnesium,
(c) 0.5 to 7 mole equivalents Lewis base,
(d) a solvating amount of a liquid hydrocarbon,
(e) wherein the mole ratios of total anionic organic groups ($R_T + R_R$), to copper and lithium minus the equivalents of halide is within the following ranges:
 1. ($R_T + R_R$):Cu equivalents = 1:0.4 to 1:0.6
 2. ($R_T + R_R$):Li⁺(Li⁺ = total Li equivalents—halide equivalents) = 1:0.4 to 1:0.6
and
(f) wherein the mole ratios of total anionic organic groups ($R_T + R_R$), to total lithium is within the following range:
($R_T + R_R$):total Li equivalents = 1:0.4 to 1:1.2.

2. An organometallic composition according to claim 1 wherein $R_T$ is a methyl group and $R_R$ is selected from thianaphthyl, benzothiazoyl, thiazoyl, and thienyl groups.

3. An organometallic composition according to claim 1 wherein $R_T$ is a methyl group, $R_R$ is a thienyl group and the Lewis base is tetrahydrofuran.

4. An organometallic composition according to claim 1 or 3 wherein the ratio of $R_R$ to $R_T$ is 0.6 to 3.

5. An organometallic composition according to claim 3 wherein the ratio of tetrahydrofuran to methyl groups is 2.5 to 5.

6. An organometallic composition according to claim 1 or 3 wherein the aromatic hydrocarbon is toluene.

7. An organometallic composition according to claim 1 wherein $R_R$ is from thianaphthyl.

8. An organometallic composition according to claim 1 wherein $R_R$ is benzothiazoyl.

9. An organometallic composition according to claim 2 wherein $R_R$ is thiazoyl.

10. An organometallic composition according to claim 3 wherein a mixture of lithium and magnesium are present in the ratio of 90 to 99.5 parts of lithium to 10 to 0.5 parts of magnesium.

11. A process for producing copper containing organometallic compositions characterized by (1) mixing a composition of the formula $R_RLi$, characterized in that $R_R$ is residual anionic group, with a composition of the formula $R_TLi$ characterized in that $R_T$ is a transferable anion in admixture with a liquid Lewis base and a liquid hydrocarbon to form a mixture containing $R_RLi$, $R_TLi$, a liquid Lewis base and a hydrocarbon; (2) reacting this mixture with a copper(I) salt complex at a temperature of $-100°$ C. to $75°$ C.; and (3) separating the reaction product from by products.

12. The process according to claim 11 wherein $R_RLi$ is thienyllithium, $R_TLi$ is methyllithium, the Lewis base is tetrahydrofuran, the hydrocarbon is toluene and the reaction temperature is between $25°$ and $40°$ C. and the copper (I) salt complex is $CuBr.Me_2S$.

13. The process according to claim 11 wherein that $R_RLi$ is thienyllithium, the $R_T$ anion source is a mixture of methyllithium and dimethylmagnesium in which the mole percent magnesium based on the total content of lithium plus magnesium is 0% to 12% and the copper (I) salt complex is $CuBr.Me_2S$.

14. The process according to claim 11 wherein $R_T$ is selected from methyllithium, ethyllithium, butyllithium or phenyllithium and the liquid hydrocarbon is selected from pentane, hexane, cyclohexane, heptane, toluene or cumene and the copper (I) salt complex is $CuBr. Me_2S$.

15. An organometallic composition of claim 3 wherein $R_T$ is methyl, $R_R$ is thienyl, the ratio of tetrahydrofuran to $R_T$ is 2.5 to 6.1 and the ratio of the ionic components in the organometallic composition $(R_T+R_R)^{-2}$, $Cu^+$, $Li^+$ and $Mg^{++}$ are respectively in the ratio of 1:(0.4–0.6):(0.4–0.6):(0.0–0.12), and $R_R/R_T$ is 1 to 3.

16. An organometallic composition of claim 3 wherein $R_T$ is methyl, $R_R$ is thienyl, the ratio of tetrahydrofuran to $R_T$ is 2.5 to 3.5 and the ratio of the ionic components in the organometallic composition $(R_T+R_R)^{-2}$, $Cu^+$, $Li^+$, LiX, and $Mg^{++}$ are respectively in the ratio of 1:(0.4–0.6):(0.4–0.6):(0.01–0.5):(0.0–0.12), and $R_R/R_T$ is 1 to 3.

17. An organometallic composition of claim 3 wherein $R_T$ is methyl, $R_R$ is thienyl, the ratio of tetrahydrofuran to $R_T$ is 2.5 to 6.1 and the ratio of the ionic components in the organometallic composition $(R_T+R_R)^{-2}$, $Cu^+$, $Li^+$, LiX, and $Mg^{++}$ are respectively in the ratio of 1:(0.4–0.6):(0.4–0.6):(0.01–0.5):(0.0–0.12), and $R_R/R_T$ is 1 to 3.

18. An organometallic composition of claim 3 wherein $R_T$ is methyl, $R_R$ is thienyl, the ratio of tetrahydrofuran to $R_T$ is 2.5 to 6.1 and the ratio of the ionic components in the organometallic composition $(R_T+R_R)^{-2}$, $Cu^+$, $Li^+$, LiX, and $Mg^{++}$ are respectively in the ratio of 1:(0.4–0.6):(0.4–0.6):(0.1–0.5):(0.0–0.12), and $R_R/R_T$ is 1 to 3.

19. An organometallic composition of claim 1 wherein $R_T$ is thienyl, $R_R$ is thienyl, the ratio of tetrahydrofuran to $R_T$ is 2.5 to 6.1 and the ratio of the ionic components in the organometallic composition $(R_T+R_R)^{-2}$, $Cu^+$, $Li^+$, LiX, and $Mg^{++}$ are respectively in the ratio of 1:(0.4–0.6):(0.4–0.6):(0.1–0.5):(0.0–0.12).

20. An organometallic composition of claim 1 wherein $R_T$ is ethyl, $R_R$ is thienyl, the ratio of tetrahydrofuran to $R_T$ is 1 to 2 and the ratio of the ionic components in the organometallic composition $(R_T+R_R)^{-2}$, $Cu^+$ and $Li^+$ are respectively in the ratio of 1:(0.4–0.6):(0.4–0.6).

21. An organometallic composition of claim 1 wherein $R_T$ is ethyl, $R_R$ is thienyl, the ratio of tetrahydrofuran to $R_T$ is 1.5 and the ratio of the ionic components in the organometallic composition $(R_T+R_R)^{-2}$, $Cu^+$, $Li^+$ and LiX are respectively in the ratio of 1:(0.4–0.6):(0.4–0.6):(0.01–0.04).

22. An organometallic composition of claim 1 wherein $R_T$ is butyl, $R_R$ is thienyl, the ratio of tetrahydrofuran to $R_T$ is 0.6 to 1.5 and the ratio of the ionic components in the organometallic composition $(R_T+R_R)^{-2}$, $Cu^+$ and $Li^+$ are respectively in the ratio of 1:(0.4–0.6):(0.4–0.6).

23. An organometallic composition of claim 1 wherein $R_T$ is butyl, $R_R$ is thienyl, the ratio of tetrahydrofuran to $R_T$ is 0.6 to 1.5 and the ratio of the ionic components in the organometallic composition $(R_T+R_R)^{-2}$, $Cu^+$, $Li^+$ and LiX are respectively in the ratio of 1:(0.4–0.6):(0.4–0.6):(.0.01–0.1).

24. An organometallic composition of claim 1 wherein $R_T$ is phenyl, $R_R$ is thienyl, the ratio of tetrahydrofuran to $R_T$ is 2.5 to 3.5 and the ratio of the ionic components in the organometallic composition $(R_T+R_R)^{-2}$, $Cu^+$, $Li^+$ are respectively in the ratio of 1:0.5:0.5.

25. An organometallic composition of claim 1 wherein $R_T$ is phenyl, $R_R$ is thienyl, the ratio of tetrahydrofuran to $R_T$ is 2.8 and the ratio of the ionic components in the organometallic composition $(R_T+R_R)^{-2}$, $Cu^+$, $Li^+$ and LiX are respectively in the ratio of 1:0.5:0.5:(0.1–0.2).

26. A process for producing copper containing organometallic compositions characterized by (1) mixing a reactant of the formula $R_RLi$, wherein $R_R$ is a residual anionic group containing one to 8 carbon atoms, with a reactant of the formula $R_TLi$, wherein $R_T$ is a transferable anionic group having one to eight carbon atoms, in admixture with a liquid Lewis base and a liquid hydrocarbon solvent; (2) reacting this mixture with a reactant selected from copper(I) salts or complexes of copper(I) salts which have been conditioned by being mixed with 0.01 to 0.05 mole equivalents of a compound selected from $R_TLi$ or $R_RLi$ per equivalent of copper(I), at a temperature of $-100°$ C. to $75°$ C.; and (3) separating the reaction product from the by products.

27. The process of claim 26 wherein a solvating agent is added to the copper(I) salt before adding it to the mixture containing $R_TLi$ and $R_RLi$ at a temperature of $-76°$ C. to $46°$ C.

28. The process of claim 27 wherein the solvating agent is dimethylsulfide and it is used in the amount of 0.1 to 1.5 mole equivalents per equivalent of copper(I) salt.

29. A process according to claims 26, 27, or 28 wherein the copper(I) salt is selected from copper chloride, copper bromide or copper iodide.

30. A process according to claims 26, 27, or 28 wherein $R_TLi$ is ethyllithium and the liquid hydrocarbon is hexane, cyclohexane, pentane, heptane, toluene or cumene.

31. A process according to claims 26, 27, or 28 wherein $R_TLi$ is methyllithium and the hydrocarbon is a liquid aromatic hydrocarbon.

32. A process according to claims 26, 27, or 28 wherein $R_TLi$ is methyllithium containing up to 12 mole percent dimethylmagnesium and the hydrocarbon is a liquid aromatic hydrocarbon.

33. A process according to claims 26, 27, or 28 wherein $R_TLi$ is butyllithium and the liquid hydrocarbon is hexane, cyclohexane, pentane, heptane, toluene or cumene.

34. A process according to claims 26, 27, or 28 wherein $R_TLi$ is phenyllithium and the liquid hydrocarbon is hexane, cyclohexane, pentane, heptane, toluene or cumene.

35. An organometallic composition according to claim 1 wherein $R_T$ is selected from methyl, ethyl, n-propyl, isopropyl, secondary butyl, isobutyl, tertiary butyl, 2-ethylhexyl or n-octyl.

36. An organometallic composition according to claim 1 or 3 wherein the ratio of Lewis base to $R_T$ is 2 to 6.

37. An organometallic composition according to claim 36 wherein the Lewis base is tetrahydrofuran and the ratio of tetrahydrofuran to $R_T$ is between 4 and 6.

38. An organometallic composition according to claim 1 wherein $R_R$ and $R_T$ are both thienyl.

39. An organometallic composition of claim 4 wherein $R_T$ is methyl, $R_R$ is thienyl, the ratio of tetrahydrofuran to $R_T$ is 2.5 to 6.1 and the ratio of the ionic components in the organometallic composition $(R_T+R_R)^{-2}$, $Cu^+$, $Li^+$, and $Mg^{++}$ are respectively in the ratio of 1:(0.4–0.6):(0.4–0.6):(0.0–0.12), and $R_R/R_T$ is 1 to 3.

40. An organometallic composition of claim 4 wherein $R_T$ is methyl, $R_R$ is thienyl, the ratio of tetrahydrofuran to $R_T$ is 2.5 to 3.5 and the ratio of the ionic components in the organometallic composition $(R_T+R_R)^{-2}$, $Cu^+$, $Li^+$, LiX, and $Mg^{++}$ are respectively in the ratio of 1:(0.4–0.6):(0.4–0.6):(0.0–0.12), and $R_R/R_T$ is 1 to 3.

41. An organometallic composition of claim 4 wherein $R_T$ is methyl, $R_R$ is thienyl, the ratio of tetrahydrofuran to $R_T$ is 2.5 to 6.1 and the ratio of the ionic components in the organometallic composition $(R_T+R_R)^{-2}$, $Cu^+$, $Li^+$, LiX, and $Mg^{++}$ are respectively in the ratio of 1:(0.4.0–6):(0.4–0.6):(0.1–0.5):(0-.0–0.12), and $R_R/R_T$ is 1 to 3.

42. An organometallic composition of claim 4 wherein $R_T$ is methyl, $R_R$ is thienyl, the ratio of tetrahydrofuran to $R_T$ is 2.5 to 6.1 and the ratio of the ionic components in the organometallic composition $(R_T+R_R)^{-2}$, $Cu^+$, $Li^+$, LiX, and $Mg^{++}$ are respectively in the ratio of 1:(0.4–0.6):(0.4–0.6):(0.1–0.5):(0-.0–0.12), and $R_R/R_T$ is 1 to 3.

* * * * *